United States Patent [19]

Wildman

[11] 4,443,189
[45] Apr. 17, 1984

[54] MULTI-PURPOSE ORTHODONTIC BRACKET

[76] Inventor: Alexander J. Wildman, 2440 Willamette St., Eugene, Oreg. 97405

[21] Appl. No.: 434,494

[22] Filed: Oct. 15, 1982

[51] Int. Cl.³ ............................................. A01C 7/00
[52] U.S. Cl. ......................................... 433/10; 433/13
[58] Field of Search ................................... 433/10, 11

[56] References Cited

U.S. PATENT DOCUMENTS

| | | | |
|---|---|---|---|
| 3,076,265 | 2/1963 | Moore | 32/16 |
| 3,748,740 | 7/1973 | Wildman | 32/14 |
| 3,780,437 | 12/1973 | Wildman | 32/14 |
| 3,842,503 | 10/1974 | Wildman | 32/14 |
| 3,854,207 | 12/1974 | Wildman | 32/14 |
| 4,023,274 | 5/1977 | Wallshein | 32/14 |
| 4,077,126 | 3/1978 | Pletcher | 433/10 |
| 4,209,906 | 7/1980 | Fujita | 433/11 |
| 4,227,876 | 10/1980 | Fogel et al. | 433/11 |
| 4,248,588 | 2/1981 | Hanson | 433/11 |

*Primary Examiner*—Robert Peshock
*Attorney, Agent, or Firm*—Klarquist, Sparkman, Campbell, Leigh & Whinston

[57] ABSTRACT

A multi-purpose orthodontic bracket comprises two interfitting cast parts, a body and a slider, uniquely configured to secure an arch wire to the lingual side of a tooth. The body has an arch wire slot oriented for insertion of an arch wire in a direction normal to the occlusal plane. The slider has a sliding portion slidably received in a channel extending transversely of the arch wire slot in the base of the body, and a closure member having a free end positioned to span the slot when closed. The channel is acutely angled from the depthwise plane or insertion direction of the slot. The closure member of the slider is positioned to move through such plane at an obtuse angle to it so that, during closure, its free end can either push the arch wire down into the slot or clamp it against a shoulder of the body alongside the slot. The sliding portion has two longitudinally spaced pairs of oppositely-directed side fins positioned in the channel to limit how far the slider can be opened and to enable it to pivot about the body when open to interpose the end of the closure member in the slot. The body and slider have oppositely directed wings for engagement by an elastomer O-ring or elastic to rigidly secure the arch wire in the bracket with the closure member part way closed. A leaf spring in the channel is hooked by the slider in a shearing relationship to lock the slider to secure the arch wire in the bracket in a fully closed position until the spring is depressed.

23 Claims, 18 Drawing Figures

MULTI-PURPOSE ORTHODONTIC BRACKET

BACKGROUND OF THE INVENTION

The present invention relates to orthodontic brackets and more particularly to brackets adapted for placement on the inner, i.e., lingual or palatal, sides of teeth.

Braces have long been used for straightening teeth. In general, this method of straightening teeth calls for connecting a resilient wire to the teeth by means of brackets individually attached to the teeth. Formerly, such brackets were universally applied to the outer or labial sides of the teeth, as disclosed in U.S. Pat. No. 3,076,265 to Moore and in FIG. 1 of U.S. Pat. No. 4,209,906 to Fujita. Recently, it has become common to apply the brackets to the inner of lingual sides of the teeth, thereby hiding the braces from view. A suitable method for applying braces to either the labial or the lingual sides of the teeth is disclosed in my prior U.S. Pat. No. 3,842,503.

A continuing problem in orthodontia is how best to secure arch wires to the teeth. A variety of brackets have been proposed for this purpose. One conventional form of bracket, disclosed in FIG. 3 of the Fujita patent, is commonly referred to as the "edgewise" bracket. This bracket has a unitary body having a central arch wire slot and a pair of oppositely-directed wings. An arch wire is secured in the slot by means of a wire ligature or an elastomer O-ring. This design is used on the labial side of the teeth and is not designed for use on the lingual side. Securing the arch wire in a slot with a ligature on the labial side is impractical because of the difficulties of twisting the ends of the ligature wire together, particularly inside the mouth, and of injury to soft tissues by the wire ends. Using elastomer O-rings, or elastics, in lieu of ligature wires is also impractical, particularly for securing an arch wire to the lingual sides of the front teeth. Frequently, the straightening force to be applied to the front teeth is such that an O-ring cannot hold the arch wire securely in the slot of a single bracket. This problem is most acute when it is necessary to apply torsion about the axis of a tooth. Two brackets are sometimes mounted side by side on a tooth to apply greater torque. However, the lingual sides of the front teeth are usually too narrow to affix two brackets.

Variations of the edgewise bracket are disclosed in U.S. Pat. Nos. 4,023,274 to Wallsheim and 4,227,876 to Fogel, et al. However, the latter designs are no more practical than the basic edgewise bracket for use on the lingual sides of the teeth.

Figure 4:
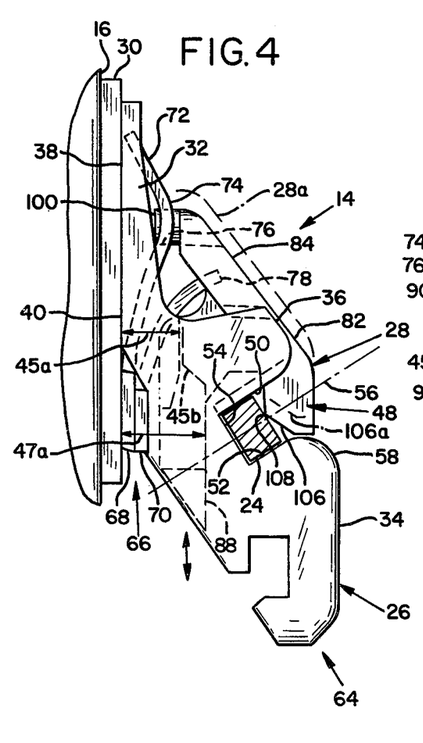
FIG. 4 is a vertically-oriented enlargement of the view of the bracket on the upper tooth of FIG. 1 showing the locking closure mode, the slider being shown part way open in phantom lines.

Another form of bracket, disclosed in FIG. 4 of the aforementioned Fujita patent, employs an arch wire slot positioned so that a wire may be inserted vertically from the opposite side of the occlusal plane, that is, from the root of the tooth toward the biting surface. Variations of this bracket are disclosed in my prior U.S. Pat. Nos. 3,748,740 and 3,854,207. This approach is not conveniently applicable to the lingual sides of the teeth because of the difficulties of inserting an arch wire into the bracket behind the teeth.

Figure 6:
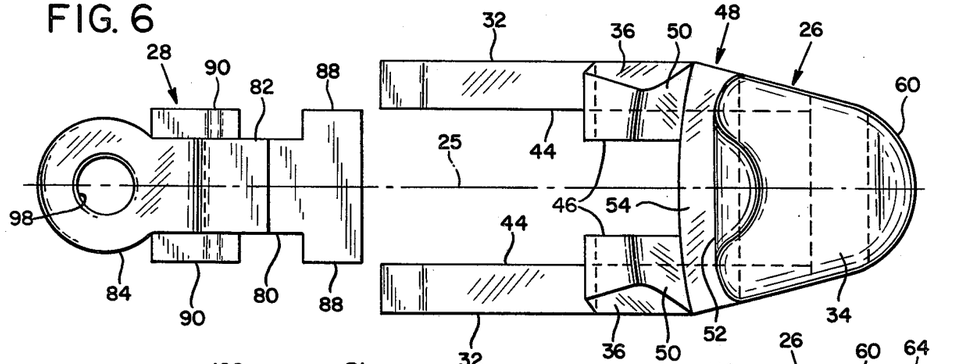
FIG. 6 is a top plan view of the bracket of FIG. 2, exploded to show the body and slider separately, the springs and elastic being omitted for clarity.

The aforementioned Fujita patent attempts to overcome some of the foregoing difficulties by proposing a lingual bracket in which the arch wire is held in a slot by means of a U-shaped spring clip. Referring to FIG. 6 of Fujita, two different kinds of bracket are used. In one kind of bracket, the slots open in a vertical direction toward the occlusal plane for use on the upper teeth. In the other kind of bracket, the slots open rearwardly, parallel to the occlusal plane, particularly for use on the lower teeth. It would be preferable to be able to use the same kind of bracket on both upper and lower teeth. A major drawback of the Fujita design is that the brackets rely primarily on the spring tension of the U-shaped clip to retain the arch wire in place. Difficulties in seating a twisted or bent arch wire squarely in the slot may make it virtually impossible to secure it with such a locking member. A further difficulty arises from the fact that the locking member is separate from the body of the bracket and, being quite small, can easily be lost in the patient's mouth while emplacing or replacing arch wires.

My prior U.S. Pat. No. 3,780,437 discloses a bracket in which the arch wire is held in a slot in the bracket body by a finger of a rigid U-shaped sliding closure member or follower. The finger has a camming portion adapted to push the arch wire downwardly into the slot as the follower is moved normal to the depthwise dimension of the slot. The follower is also connected to the bracket body by means of a snap ring which surrounds the bracket body and engages shoulders of the follower between its ends to hold the follower weakly in an open position and more strongly in a closed position. However, it is not always possible or desirable to fully seat the arch wire in its slot. Under certain circumstances, it is desirable to be able to secure the arch wire to the bracket in a position only partially seated in the slot, for example, at a depthwise angle in the slot. However, like the brackets of Fujita, this bracket does not afford a capability of partially closing the follower.

U.S. Pat. No. 4,248,588 to Hansen discloses a bracket generally similar to that of my aforementioned U.S. Pat. No. 3,780,437, except that the closure member is a resilient rather than a rigid member. Hansen also dispenses with the need for a snap ring by forming the body of the bracket so as to hold the closure member in an open and a closed position without separating it from the body. The resiliency of the member allows somewhat more flexibility in seating a bent arch wire in the slot, but does not enable it to be positioned to partially close the slot. It remains necessary to seat the wire most of the way into the slot so that it can be resiliently clamped between the legs of the follower as shown in FIG. 8 of Hansen. It would be preferable to be able to secure the arch wire to a bracket even if it cannot be seated in the slot. From FIG. 8 of Hansen, it is apparent that this goal can only be accomplished in the bracket of Hansen by using a ligature wire. As previously discussed, using such a wire is undesirable because of the difficulties of working with wire on the lingual side of the teeth, as well as the discomfort of wire ends to the soft tissues of the mouth.

In addition, both the bracket of my prior U.S. Pat. No. 3,780,437 and the bracket of Hansen are designed for use on the labial sides of the teeth. The labial sides of the teeth are essentially parallel to the axes of the teeth and, when the teeth are properly positioned, approximately normal to the occlusal plane. Hence, the arch wire slot opens frontally, normal or, as disclosed in Hansen, at slight angular variations from normal to the labial sides of the teeth, and the follower channel is essentially normal to the slots. This arrangement cannot be conveniently applied to the inner sides of the teeth, particularly to the palatal sides of the upper teeth. The inner sides of the teeth are inclined so as to intersect the occlusal plane at a large acute angle, typically of about 55°, but commonly varying over a range of 30° to 80°. This problem is acknowledged in Fujita at FIG. 6, which shows a palatal bracket opening downwardly, perpendicularly to the occlusal plane. However, as noted above, the approach of Fujita is preferably to be avoided because it requires two types of brackets. Fujita also acknowledges, in column 5, that insertion of the arch wire parallel to the occlusal plane presents some difficulties in operation and may cause deformation of the arch wire, which is desirably avoided. Thus, the problem remains of how best to position an arch wire slot and its closure means in a lingual bracket.

Accordingly, a need remains for an orthodontic bracket which overcomes the foregoing problems and limitations.

SUMMARY OF THE INVENTION

One object of the invention is to improve upon prior orthodontic brackets and, more particularly, to facilitate the use of lingual arch wires.

A second object of the invention is to provide a two-part orthodontic bracket which is functional in a partly closed position to secure an arch wire in the bracket.

Another object is to provide a lingual bracket design which enables arch wires to be inserted in a direction normal to the occlusal plane whether the brackets are mounted on upper or lower teeth.

A further object is to provide a bracket designed to rigidly secure an arch wire in or at the entrance to an arch wire slot without deforming the wire.

Yet another object is to secure arch wires to such brackets regardless of twists or bends in the wire which preclude insertion fully into an arch wire slot.

An additional object is to rigidly secure an arch wire in a bracket using elastics and, more particularly, to interchangeably secure an arch wire in a bracket either by locking the bracket or by means of elastics.

One aspect of the invention provides for an articulated winged orthodontic bracket. Such a bracket has a body including a slot and a first wing normal to the slot, a closure means including a second wing oppositely directed from the first wing and a rigid closure member for spanning the slot, and articulation means for movably interconnecting the body and closure means so that looping an elastic over the wings urges the closure means and body together to close the slot. This arrangement enables rigidly clamping the arch wire into the slot or against its side even by an elastic so as to effectively resist, for example, torsional forces of the wire. The articulation means can be a sliding or pivoting member integrally formed as part of the closure means and received in a channel or hinge structure in the body. Preferably, such member is formed so as to be both slidable to a first closed or partially closed position and pivotable to a second closed position. The closure member is preferably positioned at a radial distance from the pivoting member such that a mechanical advantage is obtained to maximize the clamping force of such member when closed by an elastic.

A second aspect of the invention provides a lingual bracket adapted for mounting on the lingual side of either the upper or lower teeth and with which the arch wire can be inserted normally to the occlusal plane. This bracket comprises a body defining an arch wire slot and a slider including a closure member and a sliding member slidably received for lengthwise movement in a channel in the body. The slot has an insertion direction intersecting the direction of movement of the sliding member in the channel at a large acute angle, preferably in the range of 38°-78°. The closure member is positioned so as to move translationally to push the arch wire downward into the slot so as the member is moved to a closed position. Such member can have an end face paralleling an opposed shoulder of the slot to enable rigidly clamping an arch wire, which may be bent or twisted so that it does not fit the slot, at the entrance to the slot. It can further include an underface intersecting the end face at an angle such that a single slider can be used with slots having different insertion angles.

A third aspect of the invention provides for a bracket having a positive locking mechanism which does not rely on the resiliency of a spring for its locking action. Such a bracket comprises a body slotted for an arch wire, a slider movable in a channel in the body, first flat spring means extending across the channel and fixed lengthwise of the body, and locking means for interengaging the spring means and the slider in a shearing relationship to lock the slider in a closed position. The spring means is deflectable downward to disengage from the locking means. An upwardly-curved second flat spring means can be provided beneath the sliding member within the channel to yieldably pivot the slider upwardly, when open, about pivot means at the end of the sliding portion.

The foregoing and other objects, features and advantages of the invention will become more readily apparent from the following detailed description of a preferred embodiment and several alternative embodiments of the invention, which proceeds with reference to the accompanying drawings. In the figures of alternative embodiments, parts corresponding to like parts of the preferred embodiment are identified by like reference numerals incremented by multiples of 100.

DETAILED DESCRIPTION OF PREFERRED EMBODIMENTS

Figure 1:
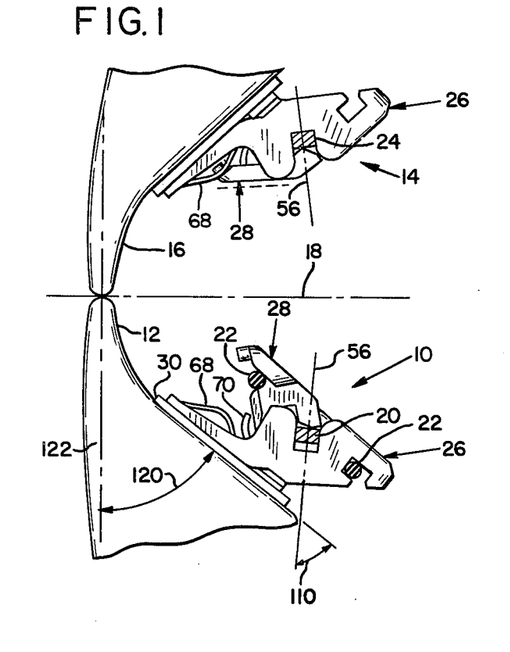
FIG. 1 is a side elevational view of a pair of upper and lower incisors fitted with lingual orthodontic brackets in accordance with the present invention.

FIG. 1 Embodiment

Referring to FIG. 1, a bracket 10 is mounted on the inner or lingual side of a lower incisor 12. A second bracket 14 is mounted on the inner side of an upper incisor 16. Incisors 12, 16 meet at occlusal plane 18. Brackets 10 and 14 have substantially identical structures, but are illustrated in two different modes of usage. An arch wire 20 is secured in bracket 10, operating in an elastic closure mode, by an elastomer O-ring or elastic 22. A second arch wire 24 is secured in bracket 14, operating in a locking mode, by a locking mechanism explained hereinafter. Since brackets 10, 14 are substantially identical in structure, the same reference numerals are used for like parts on each bracket.

Figure 2:
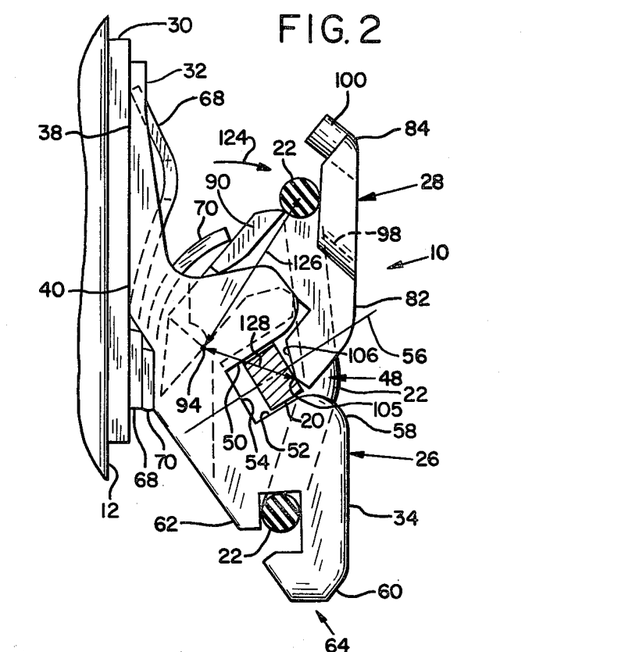
FIG. 2 is an enlarged side elevational view, oriented vertically, of the bracket on the lower tooth of FIG. 1, showing an intermediate step of the elastic closure mode, portions of the elastic being cut away for clarity.

Referring to FIG. 2, the bracket 10 comprises a bracket body 26 and a slider 28. The bracket body is mounted on a pad 30 affixed by a suitable adhesive (not shown) to the surface of the tooth. The body and slider are cast as separate integral parts and are composed of stainless steel 17-4 or other suitable alloy to provide substantial rigidity and strength in very small size parts, for example, 0.225 inches overall length, for body 26.

Figure 7A:
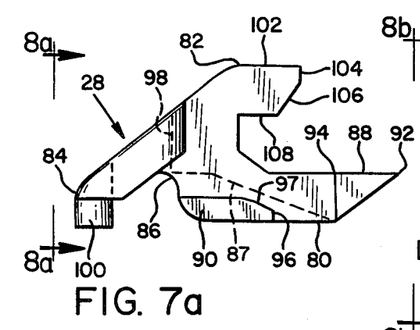
FIGS. 7a and 7b are side elevational views, oriented horizontally, of the slider and body, respectively, of FIG. 6.
Figure 7B:
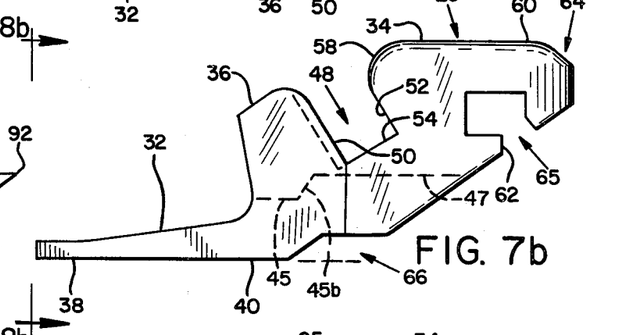
Figure 8A:
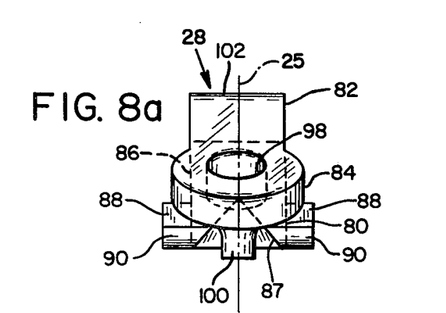
FIGS. 8a and 8b are end elevational views taken along lines 8a—8a and 8b—8b, respectively, in FIG. 7.
Figure 8B:
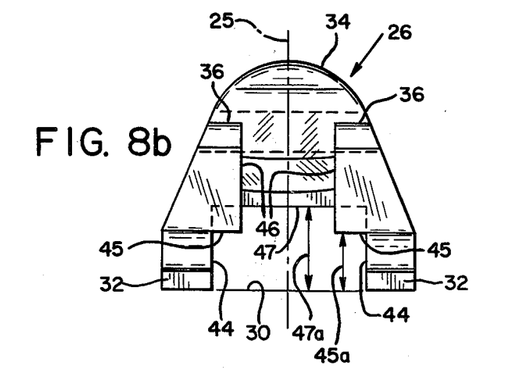

For convenience, directional references in this description refer to the horizontal orientation shown in FIGS. 7 and 8. For example, the forward or head end of the bracket is at the right and its lower side, along which it is mounted on pad 30, is at the bottom of FIG. 7b. Similarly, lateral or side-to-side dimensions are shown in FIGS. 8a and 8b.

Bracket Body Structure

Referring to FIGS. 2 and 7b, body 26 comprises a pair of laterally-spaced, parallel tails 32 for securing the body to pad 30; a head portion 34 extending in the opposite direction of the tails and elevated from pad 30; and a pair of laterally-spaced projections 36 protruding upwardly from the proximal ends 40 of the tails midway between the distal ends of the tails and head, respectively. The tails lie in the same plane to provide contact surfaces 38 along the lower side of the bracket for attachment to pad 30.

Bracket 10 is substantially symmetrical about a longitudinal centerline 25, as shown in FIGS. 6 and 8. The tails are spaced equidistantly apart about centerline 25 to define an entrance to a parallel-sided, longitudinal slider channel 44 extending along the upper surface of pad 30 into the body beneath projections 36 and head 34. Projections 36 extend inwardly over the channel and have inwardly-opposed parallel faces 46 spaced equidistantly apart about centerline 25 to define a vertical slot perpendicular to and somewhat narrower than channel 44.

Beneath projections 36 on each side of slot 46, the channel has a surface 45 spaced from pad 30, a distance indicated by arrow 45a in FIGS. 4 and 8b. Proceeding forwardly of surfaces 45, the body forms a ceiling 47 over the entire width of the channel. Ceiling 47 is parallel to and elevated from surfaces 45 a somewhat greater distance, indicated by arrow 47a, above pad 30. Surfaces 45, 47 are diagonally interconnected by a short wall segment 45b, best seen in FIG. 7b, inclined upwardly and forwardly from surface 45 to meet surface 47 at an obtuse angle.

An arch wire slot 48 extends transversely of the body, intersecting slot 46 between projections 36 and head 34. The projections 36 have frontal faces 50, which define a slightly concave front sidewall 50 of slot 48, and head 34 has a slightly convex rear face 52 paralleling face 50, which defines the opposite or rear sidewall of slot 48. The slot has a bottom wall 54 which extends between sidewalls 50, 52 and normal thereto.

Referring to FIGS. 1 and 2, a direction of insertion of an arch wire 20, 24 into slot 48 is defined by line 56, parallel to walls 50, 52 and spaced midway between them. When the wearer's mouth is open, such line is substantially normal to occlusal plane 18. The orientation of the slot is further discussed hereinafter with reference to FIG. 5.

The head 34 of the bracket body 26 has a generally rounded rearward shoulder 58 extending upwardly from sidewall 52 and curving forwardly away from the arch wire slot. The head then gradually contours, proceeding away from the slot, into a downwardly-curved, L-shaped hook 60 forming the distal end of the head. A projection 62 extends forwardly and upwardly along the underside of body 26 at an angle from the pad 30 to form, together with hook 60, a downwardly-opening, rectangular catch 65. The front end of bracket body 26 thus forms a wing 64 on one side of the arch wire slot 48 for interchangeably receiving elastic 22, when used in the elastic closure mode, or an auxiliary arch wire (not shown) when used in the locking mode.

Figures 3, 5:
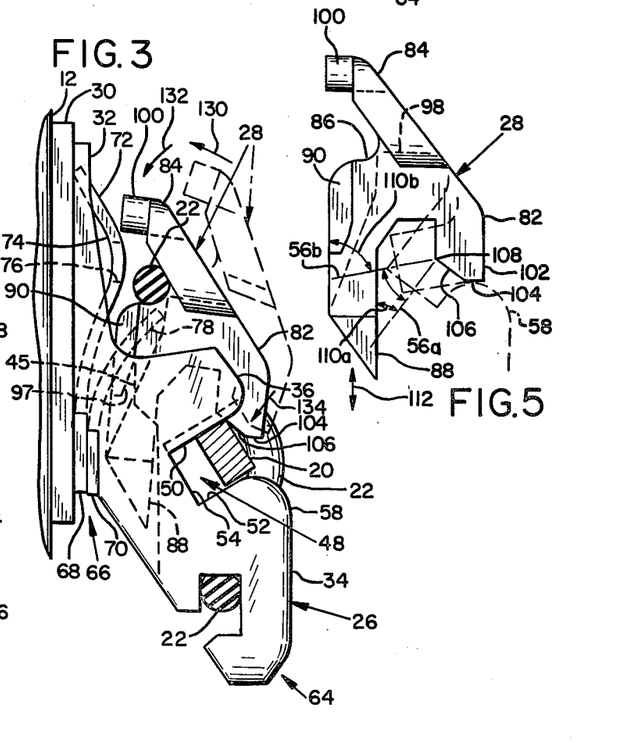
FIG. 3 is another enlarged view of the bracket of FIG. 2 showing partial closure of the entrance to the arch wire slot in the elastic closure mode, the slider being shown during closure in phantom lines.
FIG. 5 is a side elevational view, oriented vertically, of the slider used in the brackets of FIGS. 1-4 showing the various alternative angles of the arch wire slot in dashed lines and the complementary shape of the closure member.
Figure 9A:
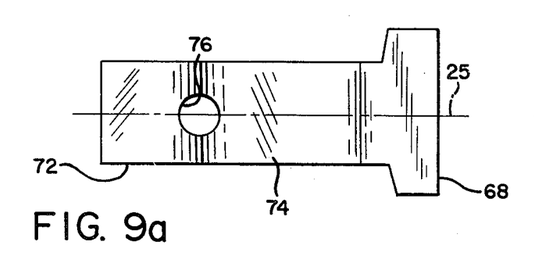
FIGS. 9a and 9b are top plan views of the springs used in the channel of the bracket of FIG. 6.
Figure 9B:
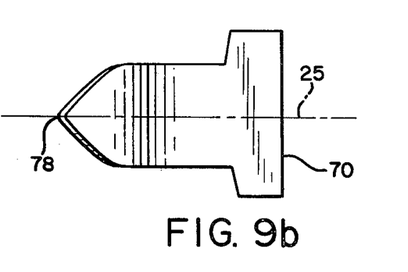

Directly under arch wire slot 48, the lateral sides of the bracket body alongside the channel are upwardly spaced from mounting surface 38 to provide a space 66 between the underside of the body and pad 30. Referring to FIGS. 2-4, the ends of a pair of leaf springs 68, 70 are sandwiched, one atop the other, between the bracket body and the pad in space 66. Both springs have a widthwise dimension extending nearly the full width of channel 44. The springs are formed of full hard stainless steel 301 and have a thickness which can vary between 0.003" and 0.006". Referring to FIGS. 9a and 9b, the springs have a generally T-shape to provide lateral flanges at one end for securing the springs in space 66.

Spring 68 extends lengthwise within channel 44 generally parallel to tails 32. It is an oil-can spring having a distal end 72 contacting pad 30 adjacent the distal ends of tails 32 and an upwardly arched portion 74 positioned midway between the proximal and distal ends of the tails. A circular hole 76 is centered in spring 68 at the top of arch 74.

Spring 70, positioned atop spring 68, extends in the same direction as spring 68 and is of the same width, but curves upwardly out of the channel rearwardly of projections 36 and tapers laterally inwardly to a point 78. The function of these springs will be better understood from a description of the slider 28, which follows.

Slider Structure

Referring to FIGS. 5, 7a and 8a, slider 28 comprises a sliding portion 80, a closure member 82 and a wing 84, all connected together at their proximal ends in a roughly T-shaped or radial pattern about a stem portion 86. Stem portion 86 has a width slightly less than that of slot 46. A V-shaped channel 87 for the pointed end 78 of spring 70 is formed in the underside of the slider. This channel is inclined lengthwise of the slider to provide a maximum depth in stem portion 86 leading into opening 98 from below.

Slide portion 80 is a generally flat member having the same lateral width as stem 86 and having two pairs of oppositely-directed fins of greater width: a pair of pivoting fins 88 at its distal end and a pair of flat fins 90 at its proximal end. Both pairs of fins have a lateral width sized to fit within channel 44.

As best seen in FIGS. 5 and 7a, fins 88 have a triangular shape, the sliding portion being beveled upwardly along its underside to a point 92 at the forward end of such member. The sliding portion 80 has a vertical thickness sized to fit slidingly within the channel above springs 68, 70. Fins 88 have a corresponding thickness and the upper rear corner 94 of such fins forms a pivot point positioned to engage against and pivot on upper wall 45b within the channel. The rear fins 90 have flat, parallel upper and lower sides. They are about half as thick vertically as fins 88 and are spaced below fins 88 so as to be able to slip out of the channel between upper walls 45 and springs 68, 70. The frontal edge faces 96 of fins 90 are spaced rearwardly from fins 88 a distance sufficient to clear projections 36 when pivot 94 of fins 88 is against wall portions 45b inside the channel, so that the slider can pivot upwardly about fins 88 when the slider is in an open position. Fins 90 each have a beveled upper face portion 97 extending a short distance rearwardly of edge face 96 to cammingly engage surfaces 45 as the sliding portion enters channel 44.

Closure member 82 and wing 84 extend in opposite directions from stem 86. Wing 84 is a generally flat annular member having a circular opening 98 centered over spring 68 forwardly adjacent hole 76. A cylindrical post 100 depends from the distal end of member 84 in position rearwardly adjacent opening 98 for insertion into hole 76 in spring 68 when the slider is fully closed, as shown in FIG. 4. Post 100 engages spring 68 in hole 76 in a shearing relationship to lock the slider in a closed position. The slider cannot be released until spring 68 is depressed, which is done by inserting a suitable instrument through hole 98 and pressing the arched portion 74 of spring 68 downwardly against pad 30.

Closure member 82 has a distal end portion 102 which is angled downwardly from the lengthwise dimension of members 82, 84 at an obtuse angle so as to project slightly downwardly into arch wire slot 48. End portion 102 has a blunt end face 104 which abuts or nearly abuts shoulder 58 when the slider is fully closed, as shown in FIG. 4. Such portion also has a beveled underface 106 truncating what would otherwise be a rectangular profile of end portion 102 along its lower distal corner to form an obtuse angle corner 108 which is approximately centered in slot 48 when the slider is closed.

Referring to FIGS. 1 and 5, arch wire slot 48 is positioned so that the direction of insertion of an arch wire, indicated by line 56, lies at an acute angle 110 to the direction of movement of sliding portion 80, indicated by arrow 112, within channel 44. Angle 110 is varied as needed from one bracket to another to orient the insertion direction 56 substantially normal to the occlusal plane 18 and thereby adapt the brackets to teeth having different slopes along their inner sides. A set of brackets will include one model of bracket 10 wherein angle 110 is approximately 55°, as illustrated in FIG. 1, and a number of different models, each having its insertion direction 56 oriented at a slightly different acute angle 110a, 110b from the direction of movement 112 of sliding portion 80. In one preferred example, five different models are provided which are essentially identical except that the insertion angle varies in increments of 10° from about 38°, as indicated by arrow 110a in FIG. 5, to about 78°, as indicated by arrow 110b. As angle 110 is varied, the position of the arch wire slot is pivoted about point 108 on the underside of the closure member 82, so that a single configuration of slider 28 can be used without modification in brackets encompassing all of the various aforesaid angles.

Operation of FIG. 1 Embodiment

As shown in FIGS. 1–4, brackets 10, 14 can be used in either of two modes. Whichever mode is to be used, the brackets are mounted on the inner sides of the teeth by cementing pads 30 to the surfaces of the teeth. The brackets are individually selected for each tooth based on the slope of such surfaces. Typically, this slope lies at an angle, indicated by arrow 120, of about 55° from a vertical axis extending through the tooth normal to occlusal plane 18. This angle can vary widely, ordinarily within a range of about 30° to 80°, depending on the misalignment of the teeth. Since, in the FIG. 1 embodiment, slider 28 moves in a direction parallel to pad 30, and therefore parallel to the inner surface of the tooth, a bracket is selected for each tooth on both the upper and lower jaw which provides an arch wire slot oriented with its insertion plane 56 as close as possible to parallel to axis 122, or substantially normal to the occlusal plane 18. For a tooth having its inner surface at a typical angle 120 of 55°, the closest bracket in the aforementioned example would be that in which the insertion direction 56 lies at an angle of 58° from the direction of movement of the slider.

Once the brackets are affixed to the teeth, an arch wire is secured to the brackets of each jaw. In general, the arch wires are inserted into the arch wire slots of the brackets in a direction approximately normal to the occlusal plane and toward the roots of the teeth. The arch wires are preferably, but not necessarily, secured first to one or more of the molars at the rear of each jaw so that the arch wires can be slid forwardly and rearwardly in their brackets parallel to the occlusal plane. Then, the wire is inserted in the brackets of the front teeth.

To insert an arch wire into a bracket, spring 68 is depressed to release post 100 from hole 76 and slider 28 is slid away from body 26 to open arch wire slot 48. Fin 88 engages channel wall 45a to keep the sliding portion 80 in channel 44 when the slider is open. Spring 70 yieldably biases the slider upwardly, that is, away from the base, pivoting on point 94, as shown in FIG. 2. To insert the arch wire in the slot, wing 84 is depressed against such spring bias to retract closure member 82 from the slot, as shown in phantom lines in FIG. 3.

Referring to FIG. 4, if the arch wire 24 can be easily inserted all or nearly all of the way into the arch wire slot 48, it is secured therein by closing the slider over the slot in a locking mode. This is done by pushing the wing 84 of the slider down until the slide portion 80 is aligned with channel 44 and then pushing the slider toward the head of the bracket. Beveled face 97 of fin 90 coacts with surfaces 45 in a downward camming action to aid in aligning portion 80 with the channel. As the slider's closure member 82 moves across the arch wire slot, its beveled end face 106 and edge 108 move at an angle across and downwardly into the slot to provide both a translational and a camming action to push the arch wire down into a fully seated position therein. This motion is illustrated by the phantom line profile 28a of the slider in FIG. 4, particularly emphasizing the position of beveled face 106a during closure of the slider.

To remove arch wire 24 from bracket 14, a pointed instrument (not shown) is inserted through opening 98 to depress spring 68 and thereby release post 100 from hole 76. Tilting the instrument toward the distal end of wing 84 retracts the slider from the channel so that post 100 clears hole 76. Further retracting the slider moves closure member 82 out of the entrance to the arch wire slot. When fully retracted, the slider is retained in the channel, with closure member 82 in an open position, by the engagement of fins 88 against channel wall 45b.

If the arch wire is bent, twisted or angled from the slot so that it is not possible or is undesirable to fully seat the wire in slot 48, then the wire can be secured in the bracket using the elastic mode as illustrated in bracket 10 in FIGS. 2 and 3. Referring first to FIG. 2, the arch wire is shown positioned in slot 48, but not fully seated, at an intermediate stage of insertion and locking. To reach this stage, slider 28 is fully retracted from channel 44 and allowed to pivot upwardly from pad 30, in the direction of arrow 124, about pivot point 94. To insert the arch wire in slot 48, wing 84 is momentarily depressed to retract closure member 82 from the slot and then, following insertion of the arch wire, is released to return the slider to the position shown in FIG. 2. Next, an elastic 22 is looped over wing 84, stretched lengthwise of the bracket over wing 64 and released thereunder to be held by hook 60.

The elastic increases the force tending to pivot slider 28 in the direction of arrow 124 to push arch wire 20 down in the slot. The distance from pivot point 94 to elastic 22 under wing 84, indicated by arrow 126, is greater than the distance from pivot point 94 to contact edge 106 on the closure member, indicated by arrow 128. This arrangement provides a mechanical advantage whereby the reduction in force applied by elastic 22 as it contracts is offset by the change in direction of application of that force to the slider as it pivots about point 94 to exert increasing leverage through the end of closure member 82 against the arch wire. The feature enables the arch wire to be temporarily held securely in one bracket while it is being positioned in other brackets. If adjustments in wire position are needed, the wire is easily released by momentarily depressing wing 84.

Once the arch wire is positioned as desired, the slider 28 of bracket 10 is moved from its intermediate closure position in FIG. 2 to a final closure position, as shown in FIG. 3. This movement is initiated by depressing wing 84. Doing so rotates the slider about pivot point 94 in the direction of arrow 130 to the position shown in phantom lines in FIG. 3. At that position, the frontal edge faces 96 of fins 90 pass below the level of the undersides 45 of projections 36, allowing fins 90 to enter channel 44. The tension of the elastic 24 thus urges the slider into the channel in an over-center action. Camming engagement of beveled faces 97 with undersides 45 causes the entry of the fins into the channel to be gradual. Hence, as the wing 84 is pushed down further, the slider moves in a compound rotating and sliding action, as indicated by arrow 132, until it is positioned as shown in solid lines in FIG. 3.

As the slider moves in the foregoing manner, the end 104, 106 of the closure member 82 initially retracts from slot 48, as indicated in dashed lines, and then moves across and depthwise part way into the slot to clamp the arch wire therein. As the fins 90 slide into the channel, the aforementioned camming action pulls the slider down against springs 68, 70, at the same time further clamping the arch wire into the slot, as indicated by arrow 133. Although some of the holding force is provided by elastic 22 stretched over the arch wire, the wire is primarily secured rigidly in slot 48 by closure member 82, rather than solely by the elastic, as in the prior art edgewise brackets. The elastic mode of closure can be used even when the arch wire 24 cannot be positioned in the slot at all by clamping it between the blunt end face 104 of the closure member and shoulder 58 of head portion 34. This clamping force is augmented by the additional tension imparted in the elastic by its further deflection from a straight line resulting from the positioning of the arch wire outside the arch wire slot. These two forces combine to hold the arch wire quite securely in the bracket even though it is not seated in the arch wire slot.

To remove arch wire 20 from bracket 10, the slider is returned to the position shown in FIG. 2 and elastic 22 is removed by slipping it over hook 22. Wing 84 is then pressed down against the gentle upward bias of spring 70 until closure member 82 is clear of the arch wire slot.

Because the bracket body and slider are articulatedly interconnected so that the wing can be moved away from the pad to apply an elastic, it is unnecessary to provide clearance beneath wing 84, when depressed, for applying an elastic, as in the prior art edgewise bracket. Hence, the portion of the bracket positioned nearest the incisal end of the tooth, particularly wing 84, can lie close to the surface of the tooth, when the bracket is closed, minimizing interference between brackets on the upper teeth and the incisal ends of the lower teeth. Additionally, in the elastic closure mode, mastication tends to urge the slider in each bracket toward the closed position in which the arch wire is fully seated, aiding in gradually moving the tooth on which the bracket is mounted to its intended position.

Figure 10:
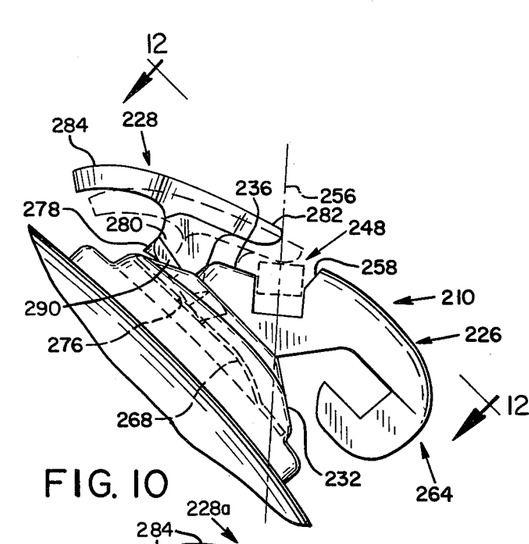
FIGS. 10 and 11 are side elevational views of a second embodiment of a bracket in accordance with the invention in various stages of closure, FIG. 11 being oriented vertically.

FIG. 10 Embodiment

In overall arrangement, bracket 210 of FIGS. 10–13 resembles bracket 10. Body 226 is of the same general shape as body 26 but lacks the long tails 32, having instead a two-part base portion 232 extending forwardly beneath wing 264 on opposite sides of the slider channel. Projections 236 do not protrude upwardly as far as do projections 36 in bracket 10. Arch wire slot 248 is thus somewhat shallower than slot 48 and closure member 282 is wider than stem portion 280, so as to laterally overlap projections 236. Also, shoulder 258 is beveled rather than rounded and hook 264 is J-shaped. The insertion direction 256 into slot 248 can be varied in the same manner as direction 56 in bracket 10. The principal remaining difference between the bodies of the two brackets is that bracket 210 employs a single leaf spring 268 welded to pad 230 at the forward end of the channel. This spring is somewhat shorter than spring 68, is biased upwardly along its entire length, and has a hole 276 corresponding to hole 76 positioned near its rearward end directly below projections 236.

Figure 11:
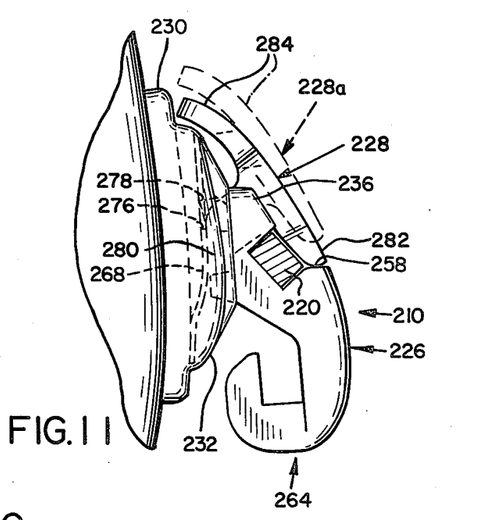
Figure 12:
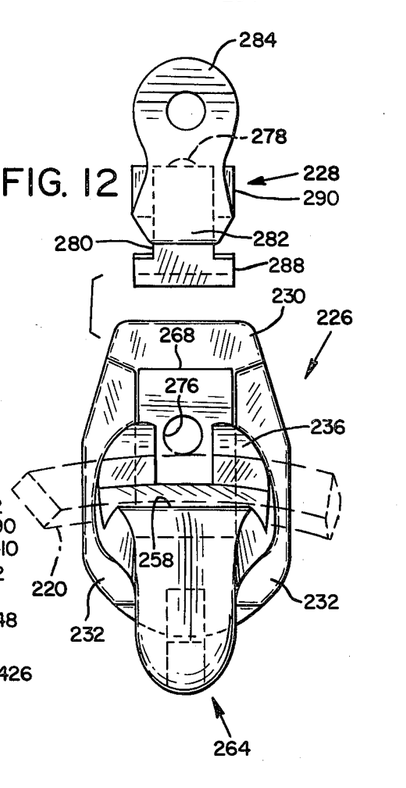
FIG. 12 is an exploded top plan view of the bracket of FIGS. 10 and 11.

The overall structure of slider 228 is likewise generally similar to that of slider 28. However, instead of post 100 located at the distal end of the wing, a tab or post 278 projects downwardly from the rear end of slide portion 280 in position to engage hole 276 when the slider is in a closed position, as best seen in FIG. 11. The closure member 282 also differs from its counterpart 82 in bracket 10 in that it extends substantially parallel to wing 284 over its entire length. Both the wing and closure member are positioned at an acute angle to slide portion 280. Like brackets 10, 14, the closure member moves translationally into the arch wire slot during closure but, lacking the beveled faces 97 on the rear fins, of slider 228, without a camming action between the slider and channel, as in bracket 10.

Figures 10A, 13, 14:
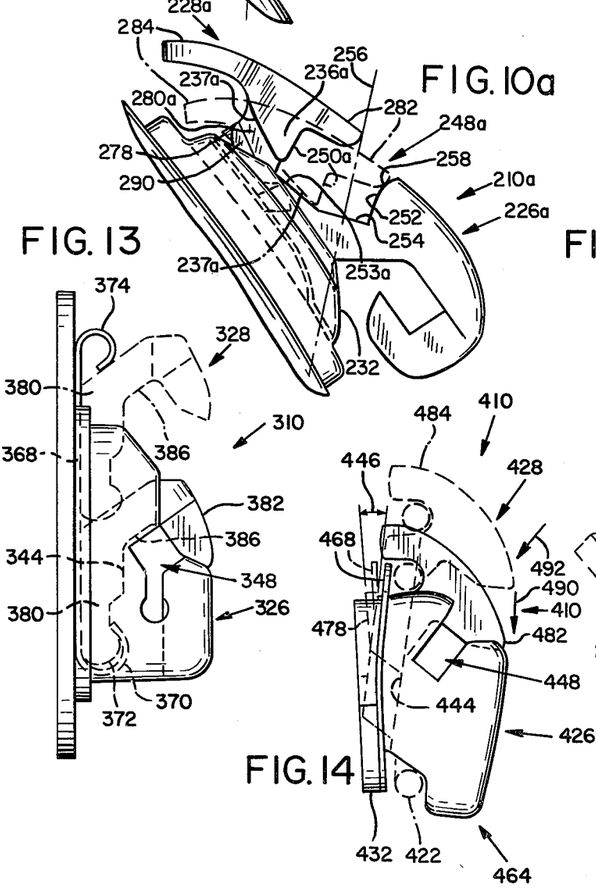
FIG. 10a is a side elevational view of a variation of the bracket of FIGS. 10-12 configured to provide a variable width arch wire slot.
FIGS. 13 and 14 are vertically-oriented side elevational views of third and fourth embodiments, respectively, of a bracket in accordance with the invention, the slider being shown in phantom lines in an open position.

Referring to FIG. 10a, bracket 210a is a variation of bracket 210 configured to provide an arch wire slot 248a of variable width. For the most part, the structure of bracket 210a is identical to that of bracket 210. However, projections 236 are deleted in bracket body 226a, leaving slot 248a with no rear wall, only a front wall 252 and bottom wall 254. A pair of approximately coplanar flat upwardly-facing surfaces 253 connecting to bottom wall 252, are formed in body 226a where the projections 236 were deleted. These surfaces are inclined to provide a smooth transition to bottom wall 252. Slider 228a is modified to provide its stem 280a with a laterally enlarged upper portion 236a on each side to substitute for projections 236 in providing a rear wall 250a for the arch wire slot. Portions 236a terminate along stem 280a at downwardly facing surfaces 237a approximately parallel to and spaced above fins 290 a distance sufficient to clear surfaces 253a when the slider is closed. As best seen in phantom lines, the rear wall is movable during closure of the slider to progressively decrease the size of slot 248a to a minimum width comparable to that of slot 248 in bracket 210.

In operation, brackets 210 and 210a can be used in either the locking or elastic closure mode described above for securing an arch wire in the bracket.

FIG. 13 Embodiment

Bracket 310 is a simplified form of bracket in which slider 328 is designed to be only slidingly received in channel 344. The sliding portion 380 lacks fins comparable to fins 88, 90 in bracket 10 for pivoting the slider about the channel. Slider 328 also lacks wings for closure by an elastic. Locking closure is provided by a single spring 368 positioned in channel 334 having a J-shaped hook 370 positioned at one end inside the channel to engage a knob end 372 of sliding portion 380. Spring 368 has another J-shaped hook 374 at its opposite end outside the channel for engaging slider stem portion 386 to limit the extent to which the slider can be retracted from the channel. Spring 368 does not engage the slider in a shearing relationship as in the other embodiments.

The principal features of bracket 310 are that slider closure member 382 and arch wire slot 348 are oriented as in bracket 210 at complementary acute angles to sliding portion 380. These features enable bracket 310 to be lingually mounted so that the arch wire can be inserted normal to the occlusal plane, and enables closure member 382 to move translationally, as well as in a camming action, during closure to seat an arch wire in the slot.

FIG. 14 Embodiment

Bracket 410 is generally similar to bracket 310 in lacking the pivoting feature provided in the FIGS. 1 and 10 embodiments. However, it includes a wing 464 on body 426 and a wing 484 on slider 428 in combination with the articulated relationship of the slider and body and the aforementioned complementary acute angle orientations of the closure member 482 and arch wire slot 448. This combination capitalizes on a mechanical advantage whereby contracting force of an elastic 422, indicated by arrow 490, is not directly opposed by any tendency of the arch wire (not shown) to unseat from slot 448. Any such tendency is resisted, as indicated by arrow 492, by the rigidity of the slider and its angular relationship to the channel and the elastic.

Also, rather than having a spring positioned within the channel 444, bracket 410 has a generally rectangular flat spring 468 carried on a base 432 and biased upwardly from the base at the slider end of the bracket so as to extend laterally across the channel. When the slider is in a closed position, spring 468 engages behind the sliding portion to lock it into the channel. The spring is deflected downwardly to retract the slider to open the arch wire slot. The sliding portion has, midway along its length, a downwardly-depending inclined keel 478 which engages spring 468, when the slider is retracted, to limit the extent to which the slider can be retracted from the channel. Channel 444 is also positioned at a small acute angle, indicated by arrow 446 from the plane of base 432. Angle 446 can be varied, in addition to varying the insertion angle of slot 448, to compensate for varying angles of the inner surfaces of the teeth.

Having illustrated and described the principles of my invention in a preferred embodiment and several variations thereof, it should be apparent to those skilled in the art that the invention may be modified in arrangement and detail without departing from such principles. I claim as my invention all such modifications as come within the spirit and scope of the following claims.

I claim:

1. An orthodontic bracket comprising:
    a body including a base, a first wing, and an arch wire slot in a side of the body remote from the base and extending generally normally to the wing;
    slot closure means including a second wing directed oppositely of the first wing and a rigid closure member integrally connected to the second wing and directed toward the first wing and adapted to be moved into and out of a slot-closing position;
    articulation means interconnecting the closure means and the body for relative movement of said closure member between a slot-open and a slot-closing position; and
    means on said wings for receiving an elastic element to apply a bias to said closure means to urge the rigid closure member to the slot-closing position to rigidly secure an arch wire in the bracket.

2. A bracket according to claim 1 in which the articulation means comprises a channel in the base of the body extending transversely of the arch wire slot and a slide means connected to the closure member and received in the channel for translational movement of the closure member relative to the depth of the arch wire slot.

3. A bracket according to claim 2 in which the closure member, arch wire slot, and slide means are mutually arranged so that, upon closure, the closure member moves at an angle across and depthwise into the slot to produce said translational movement and a camming action to seat the arch wire in said slot.

4. A bracket according to claim 2 including means for positively locking the slide means in a position such that the closure member fully closes the arch wire slot to rigidly secure the arch wire therein.

5. A bracket according to claim 1 in which the articulation means comprises pivoting means on the slot closure means received in the base of the body for rotational movement of the closure member relative to the arch wire slot.

6. A bracket according to claim 1 in which the slot closure means is a rigid unitary component comprising a third member proximally connected in a generally radial fashion to the second wing and the closure member and having a distal end movably received in said body to define said articulation means.

7. A bracket according to claim 1 in which the arch wire slot includes a bottom wall and a first sidewall formed in said body and the slot closure means includes means defining a second sidewall of the arch wire and, together with the first sidewall, defining the width of said slot, so that moving the slot closure means into and out of said slot-closing position varies the width of the arch wire slot.

8. An orthodontic bracket comprising:
a body including a base for mounting the bracket on a face of a tooth, an arch wire slot in a side of the body remote from the base, and a channel in the base extending transversely of the slot;
a slider including a sliding portion slidably received in the channel for movement between an open and a closed position, and a closure member rigidly connected to the sliding portion and having an end portion positioned to span the arch wire slot when the slider is in said closed position; and
locking means for releasably holding the slider in said closed position;
the closure member and arch wire slot being angled from the sliding portion and channel, respectively, such that, as the slider is moved to said closed position, the end portion of the closure member moves across the arch wire slot at an angle depthwise into the slot.

9. A bracket according to claim 8 including means for limiting the distance the sliding portion is slidable from said closed position so as to retain the sliding portion in the channel when the slider is in said open position.

10. A bracket according to claim 9 in which the limiting means includes a first pair of oppositely directed fins on said sliding portion extending widthwise of the channel and wall means in said channel for engaging the first fins to retain the sliding portion in the channel when the slider is moved to said open position.

11. A bracket according to claim 10 in which the sliding portion includes a second pair of fins sized to slide along said wall means in and out of the channel, the first pair of fins being positioned at a distal end of the sliding portion and the second pair of fins being spaced therefrom so that the slider can pivot in said channel about the first pair of fins between said open position and a second closed position.

12. A bracket according to claim 11 in which the fins of the second pair are each beveled along a face positioned for slidingly engaging said wall means so that the sliding portion is shifted a distance depthwise of the channel in a camming action as said portion slides along the wall means toward the first mentioned closed position.

13. An orthodontic bracket comprising:
a body including a base for mounting the bracket on an inner face of a tooth at an acute angle to an occlusal plane, an arch wire slot in a side of the body remote from the base, and a channel in the base extending transversely of the slot;
a slider including a sliding portion slidably received in the channel for movement between an open position and a closed position, and a closure member rigidly connected to the sliding portion and having an end portion positioned to span the arch wire slot when the slider is in said closed position, and
means for releasably holding the slider in said closed position;
the slot having an arch wire insertion direction acutely angled from the direction of movement of the slider lengthwise of the channel so as to be oriented depthwise approximately normal to the occlusal plane.

14. A bracket according to claim 13 in which said insertion direction is acutely angled relative to said direction of movement at an angle ranging between about 38° and about 78°.

15. A bracket according to claim 13 in which the sliding portion includes a pair of fins oppositely directed widthwise of the channel and the channel includes wall means for pivotally engaging the fins when the slider is in said open position so that the closure member can be rotated about the fins to a second closed position spanning the arch wire slot.

16. A bracket according to claim 15 including spring means fixed in the channel beneath the sliding portion for yieldably biasing the closure member toward said second closed position.

17. A bracket according to claim 13 in which the end portion of the closure member includes a pair of planar faces positioned to oppose a bottom wall of the arch wire slot in said closed position, said faces meeting at an obtuse angle to define a convex corner spaced between the sidewalls of the slot so that the closure member can engage along said corner an arch wire positioned in the slot.

18. A family of brackets according to claim 17 including a first said bracket in which the arch wire slot has an insertion direction at a first angle of approximately 55° from the direction of movement of the slider; a second said bracket in which the arch wire slot has an insertion direction at a second acute angle greater than the first angle, and a third said bracket fin in which the arch wire slot has an insertion direction at a third acute angle less than the first angle.

19. A bracket according to claim 13 in which the body includes means defining a sidewall of said arch wire slot opposite the end portion of the closure member in the direction of movement of the slider to said closed position, the sidewall including a convexly-formed shoulder remote from the bottom of the slot to define a convergent entrance to the slot such that closure of the slider tends to urge the arch wire downwardly into the slot.

20. A bracket according to claim 19 in which the closure member has an end face substantially parallel to an adjacent portion of the convexly-formed shoulder so that an arch wire positioned in a way that prevents seating it in the slot can be clamped against the shoulder and thereby rigidly secured in the bracket.

21. A bracket according to claim 13 in which the body and slider each include means defining a wing, said wings being oppositely directed for receiving an elastic for yieldably urging the slider toward said closed position, the means defining said wing in the body being configured to define a rectangular catch having an opening such that, absent said elastic, an auxiliary arch wire can be positioned in the catch.

22. An orthodontic bracket comprising:
   a body including a base, an arch wire slot in a side of the body remote from the base, and a channel in the base extending transversely of the slot;
   a slider including a sliding portion slidably received in the channel for movement between an open position and a closed position, and a rigid closure member positioned to span the arch wire slot when the slider is in said closed position;
   a flat spring means oriented along a plane extending widthwise of the channel and fixed relative to the base of the body, and
   means for interengaging the slider and the spring means in a shearing relationship to lock the slider in said closed position.

23. A bracket according to claim 21 in which the spring is deflectable transversely of said plane for disengaging the interengaging means so that the slider can be moved to said open position.

* * * * *